United States Patent
Simonovsky et al.

(10) Patent No.: US 10,540,781 B2
(45) Date of Patent: Jan. 21, 2020

(54) ASSISTANCE DEVICE AND METHOD FOR PROVIDING IMAGING SUPPORT TO AN OPERATING SURGEON DURING A SURGICAL PROCEDURE INVOLVING AT LEAST ONE MEDICAL INSTRUMENT

(71) Applicant: MAQUET GMBH, Rastatt (DE)

(72) Inventors: Martin Simonovsky, Karlsruhe (DE); Bastian Ibach, Karlsruhe (DE); Peter Baumung, Karlsruhe (DE); Aurelien Gauvin, Nancy (FR); Thilo Franz, Karlsruhe (DE)

(73) Assignee: MAQUET GMBH, Rastatt (DE)

( * ) Notice: Subject to any disclaimer, the term of this patent is extended or adjusted under 35 U.S.C. 154(b) by 47 days.

(21) Appl. No.: 15/653,739

(22) Filed: Jul. 19, 2017

(65) Prior Publication Data

US 2017/0352164 A1    Dec. 7, 2017

Related U.S. Application Data

(63) Continuation-in-part of application No. PCT/EP2016/051189, filed on Jan. 21, 2016.

(51) Int. Cl.
*G06K 9/00* (2006.01)
*G06T 7/73* (2017.01)
(Continued)

(52) U.S. Cl.
CPC ............... *G06T 7/73* (2017.01); *A61B 34/20* (2016.02); *A61B 90/361* (2016.02);
(Continued)

(58) Field of Classification Search
None
See application file for complete search history.

(56) References Cited

U.S. PATENT DOCUMENTS

2005/0219581 A1* 10/2005 Dobashi .................. G06K 9/38
                                                                358/1.9
2008/0058989 A1*  3/2008 Oleynikov ......... A61B 1/00149
                                                                700/259
(Continued)

FOREIGN PATENT DOCUMENTS

DE        19529950 C1    11/1996
DE        19961971 A1     7/2001

OTHER PUBLICATIONS

Reddi, S. S., et al., "An Optimal Multiple Threshold Scheme for Image Segmentation", IEEE Transactions on Systems, Man, and Cybernetics, Jul./Aug. 1984, vol. SMC-14, No. 4, pp. 661-665.

(Continued)

*Primary Examiner* — Sean M Conner

(57) ABSTRACT

Described is an assistance device for providing imaging support to an operating surgeon during a surgical procedure involving at least one medical instrument. The assistance device comprises a camera, a display unit, a manipulator coupled to the camera, a manipulator controller and an image processing unit. The image processing unit includes an instrument detection module for detecting at least one target structure that represents the instrument being used in the frame in question by identifying a predetermined distinguishing feature, and for extracting position information that indicates the position of the target structure in the frame. The instrument detection module identifies an image segment as the predetermined distinguishing feature, said image segment being characterized by a color saturation that is equal to or less than a predefined color saturation and by a contour line that delimits the image segment and has at least one rectilinear section.

13 Claims, 7 Drawing Sheets

(51) Int. Cl.
| | |
|---|---|
| *G06T 7/246* | (2017.01) |
| *A61B 34/20* | (2016.01) |
| *A61B 90/00* | (2016.01) |
| *G06T 7/136* | (2017.01) |
| *G06T 7/12* | (2017.01) |
| *G06K 9/32* | (2006.01) |
| *G06K 9/46* | (2006.01) |
| *G06K 9/62* | (2006.01) |
| *H04N 5/232* | (2006.01) |

(52) U.S. Cl.
CPC ........ *G06K 9/00711* (2013.01); *G06K 9/3216* (2013.01); *G06K 9/4604* (2013.01); *G06K 9/4652* (2013.01); *G06K 9/6202* (2013.01); *G06T 7/12* (2017.01); *G06T 7/136* (2017.01); *G06T 7/246* (2017.01); *H04N 5/23293* (2013.01); *H04N 5/23296* (2013.01); *A61B 2034/2057* (2016.02); *A61B 2034/2065* (2016.02); *A61B 2090/373* (2016.02); *A61B 2576/00* (2013.01); *G06K 2209/057* (2013.01); *G06T 2207/10024* (2013.01); *G06T 2207/10068* (2013.01)

(56) References Cited

U.S. PATENT DOCUMENTS

| | | | | |
|---|---|---|---|---|
| 2008/0122939 | A1* | 5/2008 | Hirai | H04N 5/23212 348/222.1 |
| 2012/0134536 | A1* | 5/2012 | Myokan | G06K 9/00355 382/103 |
| 2013/0272570 | A1* | 10/2013 | Sheng | G06F 3/017 382/103 |

OTHER PUBLICATIONS

Darrin R. Uecker et al: "Automated instrument tracking in robotically assisted laparoscopic surgery", Journal of Image Guided Surgery, vol. 1, No. 6, Jan. 1, 1995 (Jan. 1, 1995), pp. 308-325.

Doignon C et al: "Detection of grey regions in color images : application to the segmentation of a surgical instrument in robotized laparoscopy", Intelligent Robots and Systems, 2004. (IROS 2004). Proceedings. 2004 IEEE/RSJ International Conference on Sendai, Japan—Sep. 28 to Oct. 2, 2004, Piscataway, NJ, USA, IEEE, Piscataway, NJ, USA, vol. 4, Sep. 28, 2004 (Sep. 28, 2004), pp. 3394-3399.

Translated International Search Report (completed Apr. 29, 2016— dated May 11, 2016) which issued for corresponding international application PCT/EP2016/051189, 2 pages.

* cited by examiner

ASSISTANCE DEVICE AND METHOD FOR PROVIDING IMAGING SUPPORT TO AN OPERATING SURGEON DURING A SURGICAL PROCEDURE INVOLVING AT LEAST ONE MEDICAL INSTRUMENT

CROSS REFERENCE TO RELATED APPLICATIONS

The present application is a continuation-in-part filed under 35 U.S.C. § 111(a), and claims the benefit under 35 U.S.C. §§ 365(c) and 371 of PCT International Application No. PCT/EP2016/051189, filed Jan. 21, 2016, which designates the United States of America, and claims benefit of German Patent Application No. 10 2015 100 927.7, filed Jan. 22, 2015. The disclosure of each of these applications is incorporated by reference herein in its entirety.

TECHNICAL FIELD

The invention relates to an assistance device for providing imaging support to an operating surgeon during a surgical procedure involving at least one medical instrument, the assistance device comprising a camera for generating a video signal that contains a sequence of image frames, a display unit for displaying the image sequence based on the video signal, an image processing unit having an instrument detection module for detecting at least one target structure that represents the instrument being used in the frame in question by identifying a predefined distinguishing feature and for extracting position information that indicates the position of the target structure in the frame, a manipulator which is coupled to the camera and can be controlled via a control signal to move the camera, and a manipulator controller for generating a control signal from the position information and for actuating the manipulator via the control signal.

BACKGROUND

Assistance devices that effectively support an operating surgeon during a surgical procedure are known in the prior art. For instance, during a laparoscopic procedure, the surgeon views the surgical site indirectly via a display unit, for example a monitor, on which the laparoscopic instruments with which he is manipulating the anatomical structure in the patient are visible. The video image being displayed on the monitor in real time is recorded by a camera, which is part of an endoscope and is directed toward the surgical site.

During the procedure, the camera must be aimed at the surgical site in such a way that the target area being treated, along with the instrument tips and the anatomical structure to be manipulated, are located approximately at the center of the video image being displayed on the display unit. To change the image segment being viewed, the camera must therefore be moved in the body of the patient. The target area must then again be displayed at the center of the video image.

To allow the endoscopic camera to be repositioned in the desired manner, it is coupled to a manipulator, for example a robotic arm, which is adjusted in accordance with the desired camera movement. For this purpose, said manipulator is actuated by a manipulator controller via a control signal, which is obtained from the position of the instrument tip detected in the video image. An assistance device of the type described above is described, for example, in DE 199 61 971 B4.

Conventional assistance devices typically operate using markings that are attached to the instrument tip, thereby forming a distinguishing feature that allows the instrument tip to be detected in the video image. In place of such a marking, inherent characteristics of the medical instrument being used, such as its specific shape or specific color, may be used as a distinguishing feature. It is a drawback of these solutions, however, that the distinguishing feature to be identified is a characteristic peculiar to the instrument being used. Thus, it is not possible to identify any and all instruments.

SUMMARY OF THE DISCLOSURE

The object of the invention is to provide an assistance device that permits a largely automatic instrument identification, in particular without the use of markings provided specifically for that purpose.

This object is attained by the invention with an assistance device of the type described at the outset, in that the instrument detection module identifies an image segment as a predefined distinguishing feature, said image segment being characterized by a color saturation that is equal to or less than a predefined color saturation, and by an outline that delimits the image segment and has at least one rectilinear section.

The solution according to the invention is based firstly on the realization that medical instruments commonly used in the present technical field are made of largely achromatic materials, i.e. they have a color saturation that is significantly lower than the color saturation of the anatomical structure located in the target area being treated. Secondly, the invention is based on the realization that in large part, nearly every suitable instrument is a straight and rigid object. Against this background, the solution of the invention provides for the distinguishing feature that is identified by the instrument detection module to be identified as an image segment that has a comparatively low color saturation and contains an outline, at least part of which extends in a straight line. Based on this distinguishing feature, it is possible to delimit nearly any instrument in the video image from the anatomical structure present in the target area. More particularly, this can be accomplished without the use of a marking provided on the instrument.

The upper limit of the color saturation to be defined as the distinguishing feature is selected such that the measured color saturations of conventional medical instruments are reliably below this upper limit. As was mentioned above, this is possible because conventional instruments are generally made of materials that are largely achromatic and therefore have a far lower color saturation than the surrounding anatomical structure in the target area.

The image processing unit includes a segmentation module which, on the basis of the frame in question, generates at least one binary image in which the instrument detection module identifies the image segment. The pixels of this binary image take on one of two possible binary values, depending on whether or not the pixels of the frame that correspond to them have a color saturation that corresponds to the predefined distinguishing feature. In this way, a black-and-white binary image can be generated, for example, in which the white image points or pixels represent one or more instruments and the black pixels represent the anatomical structure.

In an exemplary embodiment, the image processing unit includes a preprocessing module, which generates a grayscale image on the basis of the frame in question, the pixels of said image each being assigned a grayscale value that represents the color saturation of the corresponding pixel of the frame. On the basis of the grayscale image, the segmentation module then generates the at least one binary image, the binary pixels of which are assigned a first binary value if the associated grayscale values are equal to or less than a threshold value that corresponds to the predefined color saturation, and the binary pixels of which are assigned a second binary value if the associated grayscale values are greater than the threshold value. The grayscale image generated in this embodiment is thus a color saturation image from which one or more binary images to be used as the basis for further image processing can be derived without great technical effort.

The instrument detection module combines multiple linearly spaced rectilinear sections of the outline to form a continuous edge line, which represents an edge of the instrument. This embodiment is particularly advantageous when multiple intersecting instruments are shown in the binary image assigned to the frame in question. Since it can be assumed that a given instrument has a straight shape, the instrument associated with these sections can be filtered out of the intersecting instrument arrangement, as it were, based on the composition of collinearly spaced outline sections. This facilitates instrument identification when multiple instruments are used during the surgical procedure.

To detect the target structure, the instrument detection module pairs two edge lines that are arranged parallel to one another in each case. This edge pairing is based on the fact that when multiple edge lines arranged parallel to one another are detected, there is a high probability that these edge lines belong to one and the same instrument. This enables even more reliable instrument identification.

In an exemplary embodiment, the segmentation module generates not just one, but a plurality of binary images based on the grayscale image in question, and uses different threshold values for the generation of these. Accordingly, for each of these binary images, a separate upper limit for color saturation is specified as the distinguishing feature. This is advantageous particularly when one and the same instrument is made of various materials that have different color saturations. For example, the tip of such an instrument may be made of metal while the instrument shaft is made of plastic. The same applies when multiple instruments made of different materials and thus having different color saturations are present in the frame. In such cases, if the threshold value provided for generation of the binary image is defined such that parts made of plastic can be effectively segmented in the binary image, this does not necessarily mean that the same will be accomplished with the same quality for metal parts by using the same threshold value. In that case, rather than generating a single binary image based on a single threshold value, it is advantageous to generate a plurality of binary images that are based on a corresponding plurality of threshold values. These binary images form a reliable basis for precise instrument identification, even under difficult conditions. Moreover, the generation of multiple binary images can be readily parallelized, which offers an advantage in terms of processing speed.

In an exemplary embodiment, the instrument detection module identifies mutually corresponding rectilinear sections in the binary images that have been generated on the basis of the frame in question, and combines these sections to form a single edge line that represents an edge of the instrument. In this embodiment, since the multiple binary images are generated using different threshold values, an identified outline that forms the junction between an image segment of high color saturation, which represents the anatomical structure, and an image segment of low color saturation, which represents the instrument, shifts, as it were, from binary image to binary image. When the binary images are then viewed superimposed, as it were, a spatially close arrangement of nearly parallel contour sections results, from which the edge of the instrument can be reliably deduced.

In an exemplary embodiment, the image processing unit includes a tracking module that tracks the target structure detected by the instrument detection module over a plurality of successive frames. The manipulator controller generates the control signal associated with the frame in question, using the position information for the target structure, to actuate the manipulator only if the tracking module has already tracked said target structure over multiple successive frames. Thus, only target structures that can be tracked over multiple successive frames are used to actuate the manipulator for the purpose of repositioning. A supposed identified instrument that appears in only a single frame is therefore not considered in the repositioning of the manipulator. This enables error-free and uniform manipulator repositioning.

The tracking module assigns a tracker to a target structure that is detected for the first time in the frame in question by the instrument detection module, and uses the tracker to track said target structure detected in the subsequent frames. A tracker in this context is understood as a data processing element that is used to represent an identified instrument.

In an exemplary embodiment, the image processing unit includes a flow module, which detects an optical flow of the image sequence that represents movement information contained in the image sequence. Based on the detected optical flow, it is possible to predict in which direction and at what speed the tracker associated with the identified instrument will move in the subsequent frames.

The tracking module comprises a first submodule, which is located upstream of the instrument detection module in the image processing direction, and a second submodule, which is located downstream of the instrument detection module in the image processing direction. The first submodule factors in the optical flow detected in the flow module to make a prediction regarding the position information of the tracker for the next frame, which has not yet been processed by the instrument detection module. For this next frame, which in the meantime has been processed by the instrument detection module, the second submodule verifies the prediction made by the first submodule, based on the position information about the tracker detected by the instrument detection module. This enables a particularly reliable tracking of the instrument identified in the image sequence.

The preprocessing module is designed to perform a white balance adjustment of the frame in question. This white balance adjustment counteracts potential miscalibrations that might impair instrument identification on the basis of the chromatic characteristics of the instrument, in particular its color saturation.

In an exemplary embodiment, the image processing unit includes a parameter optimization module, which processes the frames asynchronously to the preprocessing module, and from this generates actuation information that specifies to the preprocessing module whether or not it should perform a white balance adjustment. Due to the asynchronous operation of the parameter optimization module, the check to determine whether or not a white balance adjustment is necessary is implemented as a process that is carried out in parallel to the remaining image processing. For example, the check may be carried out on a sample basis, as it were, within the image sequence, for example checking only every nth frame, where n is a natural number greater than 1.

The parameter optimization module can also predefine the threshold values for the segmentation module on the basis of the asynchronous processing of the frames. This is advantageous, for example, in cases in which instruments are changed during the surgical procedure, and thus the color saturations thereof within the image sequence instantaneously change drastically. In such cases, adjusting the threshold values that correspond to the color saturations with the aid of the asynchronously operating parameter optimization module is a suitable measure for responding to such changes.

The invention further relates to a method for providing imaging support to an operating surgeon during a surgical procedure. The features described above and in the following with respect to the assistance device of the invention are also considered to be part of the method claimed.

BRIEF DESCRIPTION OF THE DRAWINGS

In the following, the invention will be described in greater detail in reference to the figures. The figures show.

DETAILED DESCRIPTION AND INDUSTRIAL APPLICABILITY

Figure 1:
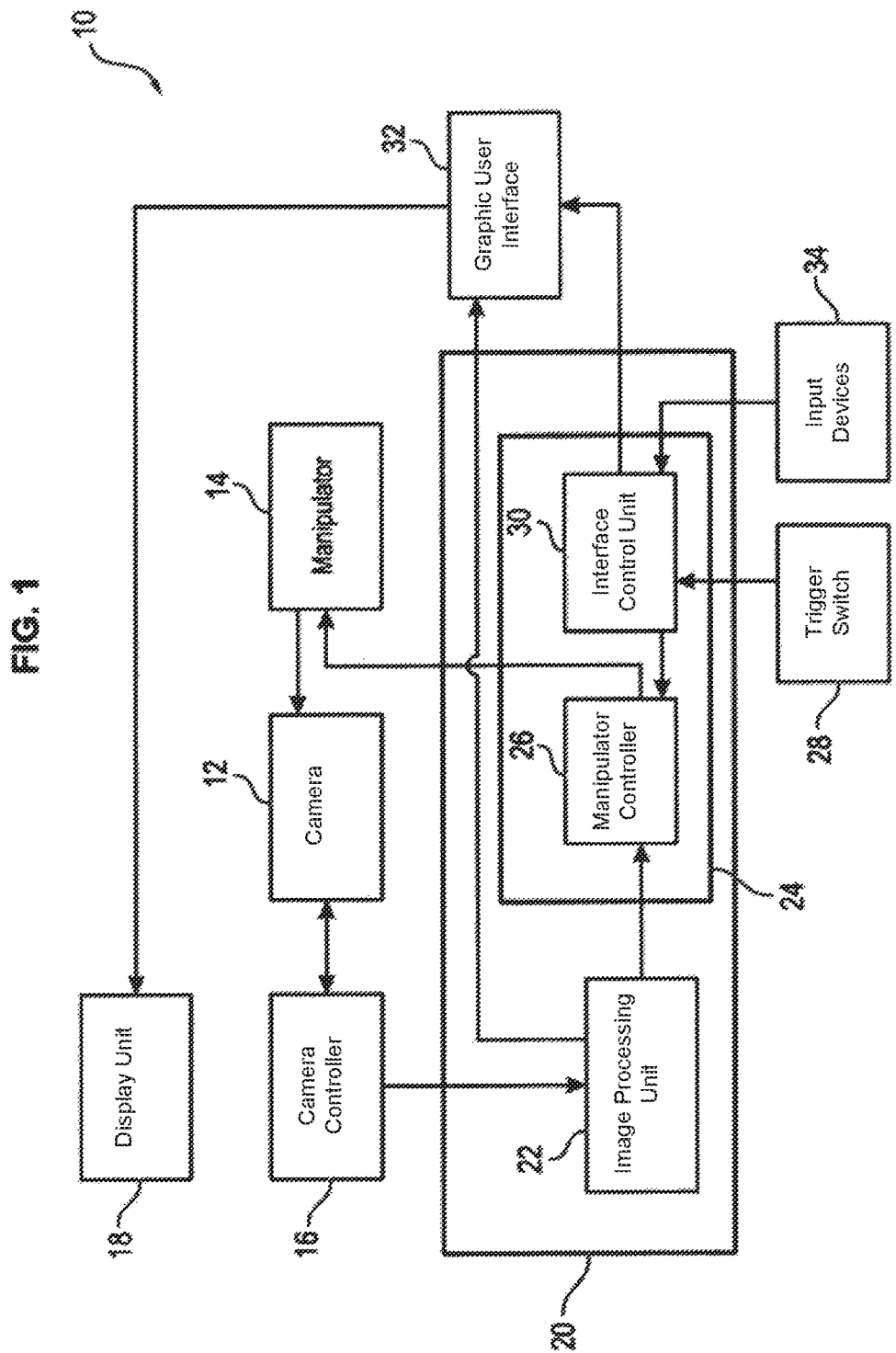
FIG. 1 is a block diagram illustrating the overall structure of an assistance device according to the invention.

FIG. 1 is a block diagram of an assistance device 10 according to the invention.

Assistance device 10 comprises a camera 12, which is part of an endoscope, not explicitly shown, which is held by a manipulator 14, for example a robotic arm. Manipulator 14 has mechanical degrees of freedom that enable a repositioning of camera 12.

Camera 12 captures a video image of a target area inside the human body in which the anatomical structure to be treated is located. Camera 12 thus generates a video signal that contains a sequence of image frames and is output in the form of a data stream to a camera controller 16. Camera controller 16 transmits the video signal to a display unit 18, for example a monitor, on which a video image of the anatomical structure being treated, corresponding to the video signal, is displayed.

Camera controller 18 feeds the video signal to a controller 20 via an image acquisition module, for example a "frame grabber", which is not shown in FIG. 1. Controller 20 includes an image processing unit 22, which uses the video signal supplied to it as an input signal for carrying out an instrument identification in a manner that will be explained in detail later. During this instrument identification, the surgical instruments that are visible in the video image are identified and tracked by the image processing unit 22. In that process, position information is obtained and is fed to a control unit 24. Control unit 24 includes a manipulator controller 26. Said controller functions as a path controller, which uses the position information supplied to it to generate a control signal, which is used to actuate manipulator 14. With this actuation, for example, the manipulator 14 repositions the camera 12 that is held on it such that the tip of an instrument in the video image being displayed on the display unit 18 is always located at the center of the image.

Assistance device 10 further has a trigger switch 28, which is coupled to an interface control unit 30 contained in control unit 24. Actuating the trigger switch 28 causes the interface control unit 30 to activate manipulator controller 26 so as to reposition camera 12.

Assistance device 10 further has a graphic user interface 32, which is coupled on one side to image processing unit 22 and interface control unit 30, and on the other side to display unit 18. Assistance device 10 further comprises additional input devices that are of minor importance for an understanding of the present invention and are generally denoted in FIG. 1 by reference sign 34.

Figure 2:
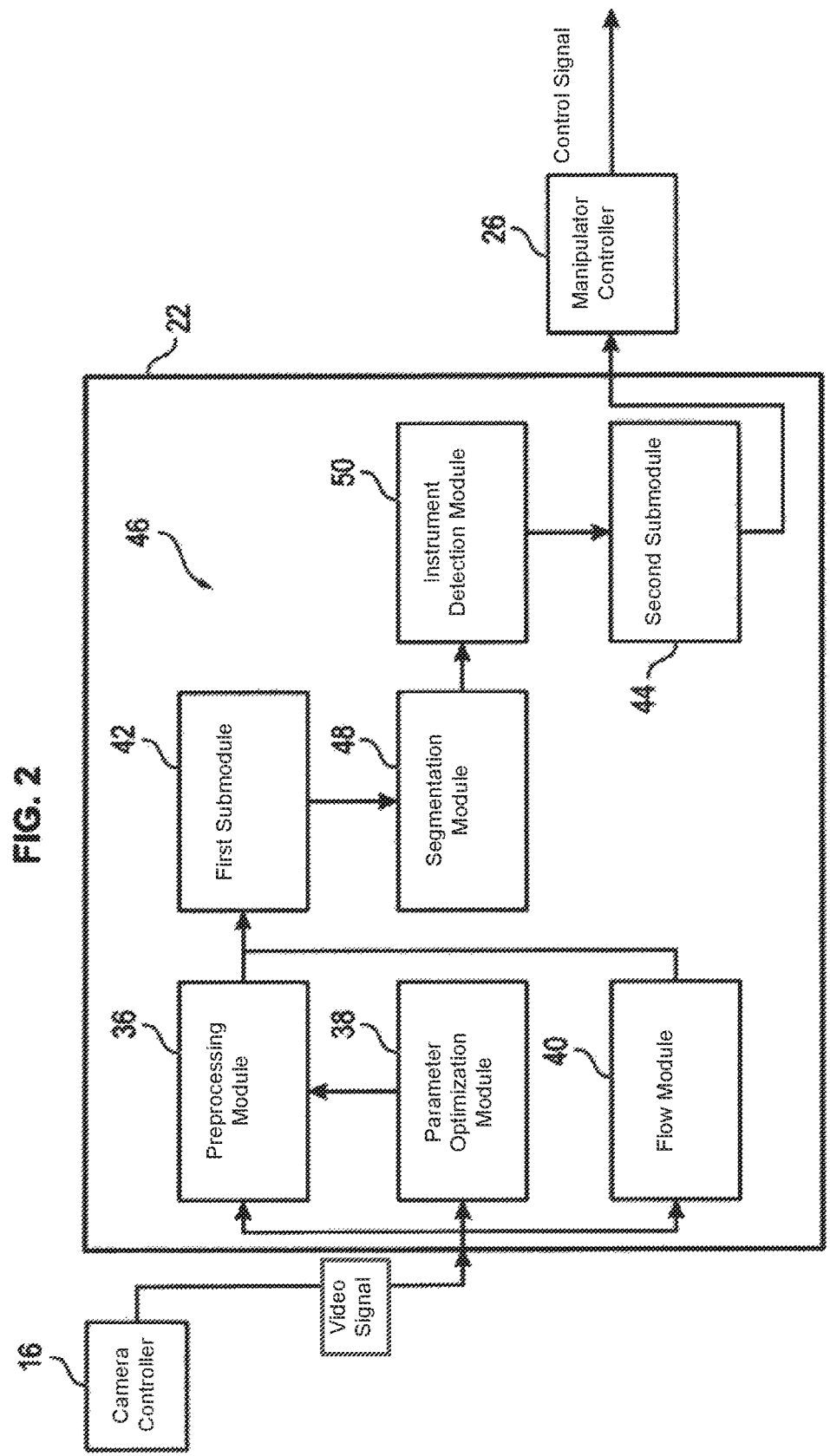
FIG. 2 is a block diagram illustrating the structure of an image processing unit of the assistance device.

FIG. 2 shows a block diagram illustrating the structure of image processing unit 22.

Image processing unit 22 includes a preprocessing module 36, a parameter optimization module 38 and a flow module 40. The video signal, which contains a sequence of image frames, is fed to each of modules 36, 38 and 40 by camera controller 16. Parameter optimization module 38 is coupled to preprocessing module 36.

Image processing unit 22 further includes a first submodule 42, which, together with a second submodule 44, forms a tracking module, denoted generally in FIG. 2 by reference sign 46. The first submodule 42 is coupled on the input side to preprocessing module 36 and to flow module 40. On the output side, it is connected to a segmentation module 48. Segmentation module 48 is in turn coupled on the output side to an instrument detection module 50. The output of instrument module 50 is coupled to the second submodule 44 of tracking module 46. Finally, the second submodule 44 forms the output of image processing unit 22 and is therefore connected to manipulator controller 26, which generates the control signal for actuating the manipulator 14 from the signal supplied to it by image processing unit 22.

Figure 3:
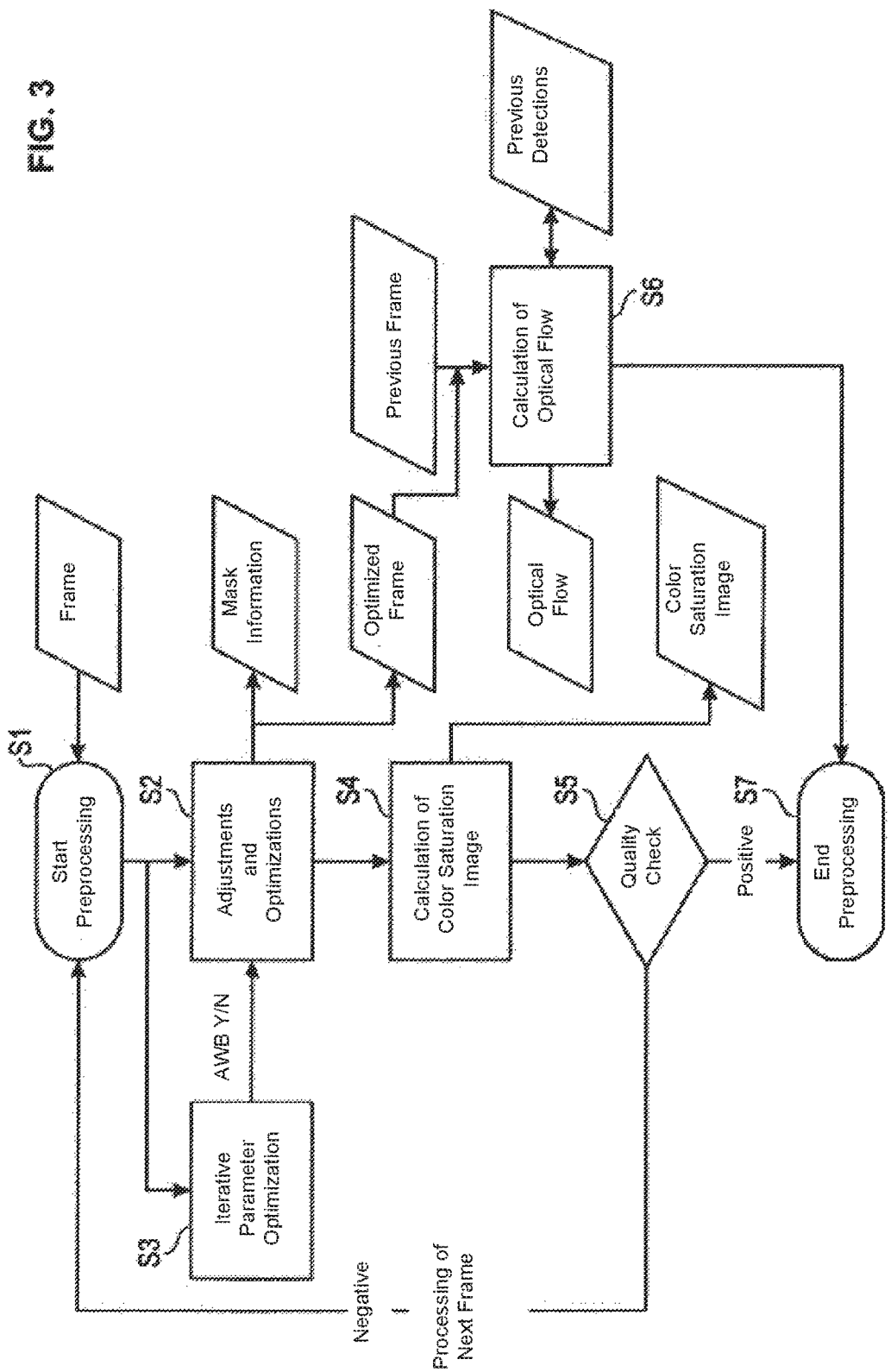
FIG. 3 is a block diagram showing the process flow of image preprocessing carried out in the method of the invention.
Figure 4:
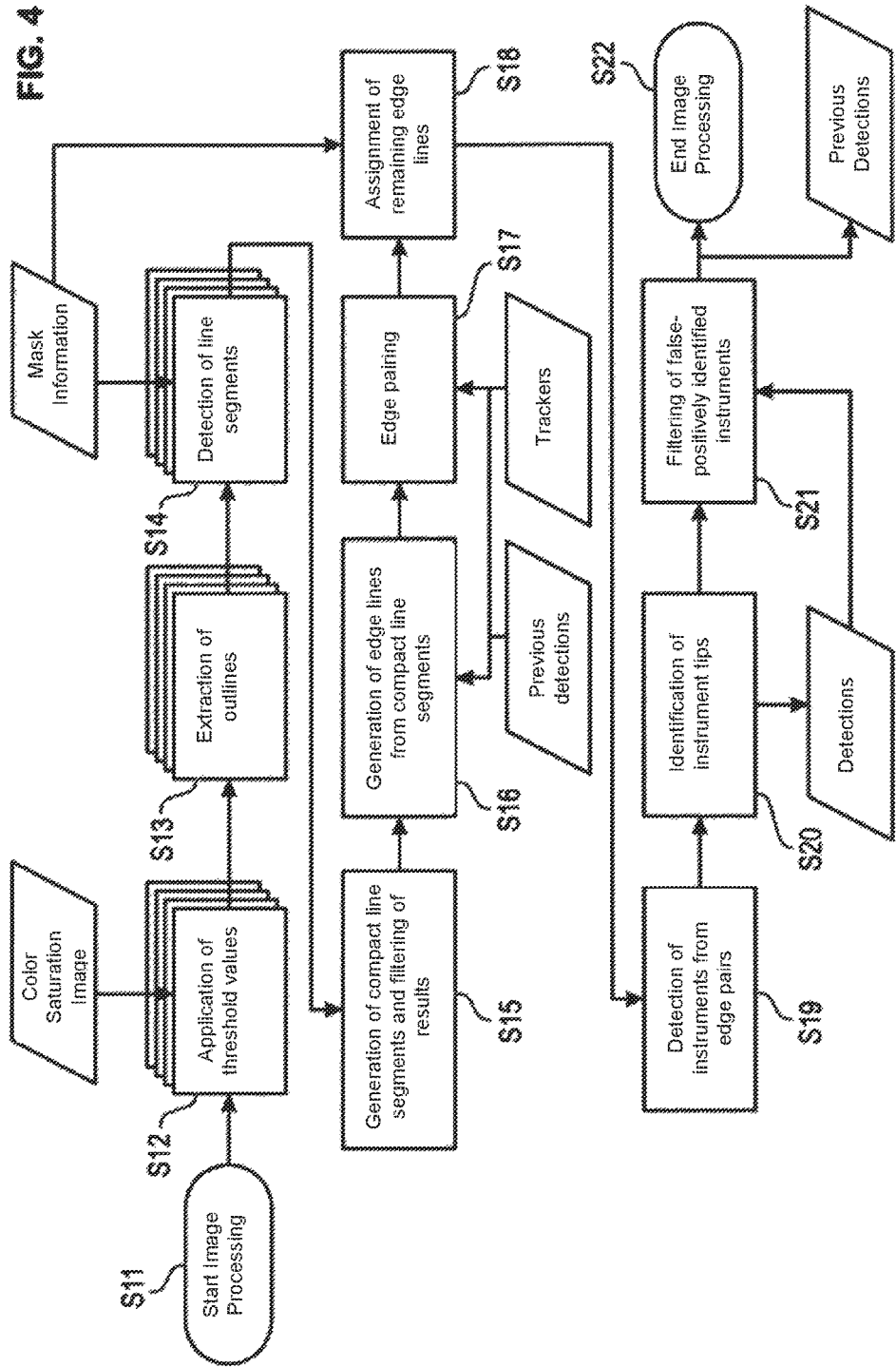
FIG. 4 is a block diagram showing the process flow of instrument detection carried out in the method of the invention.
Figure 5:
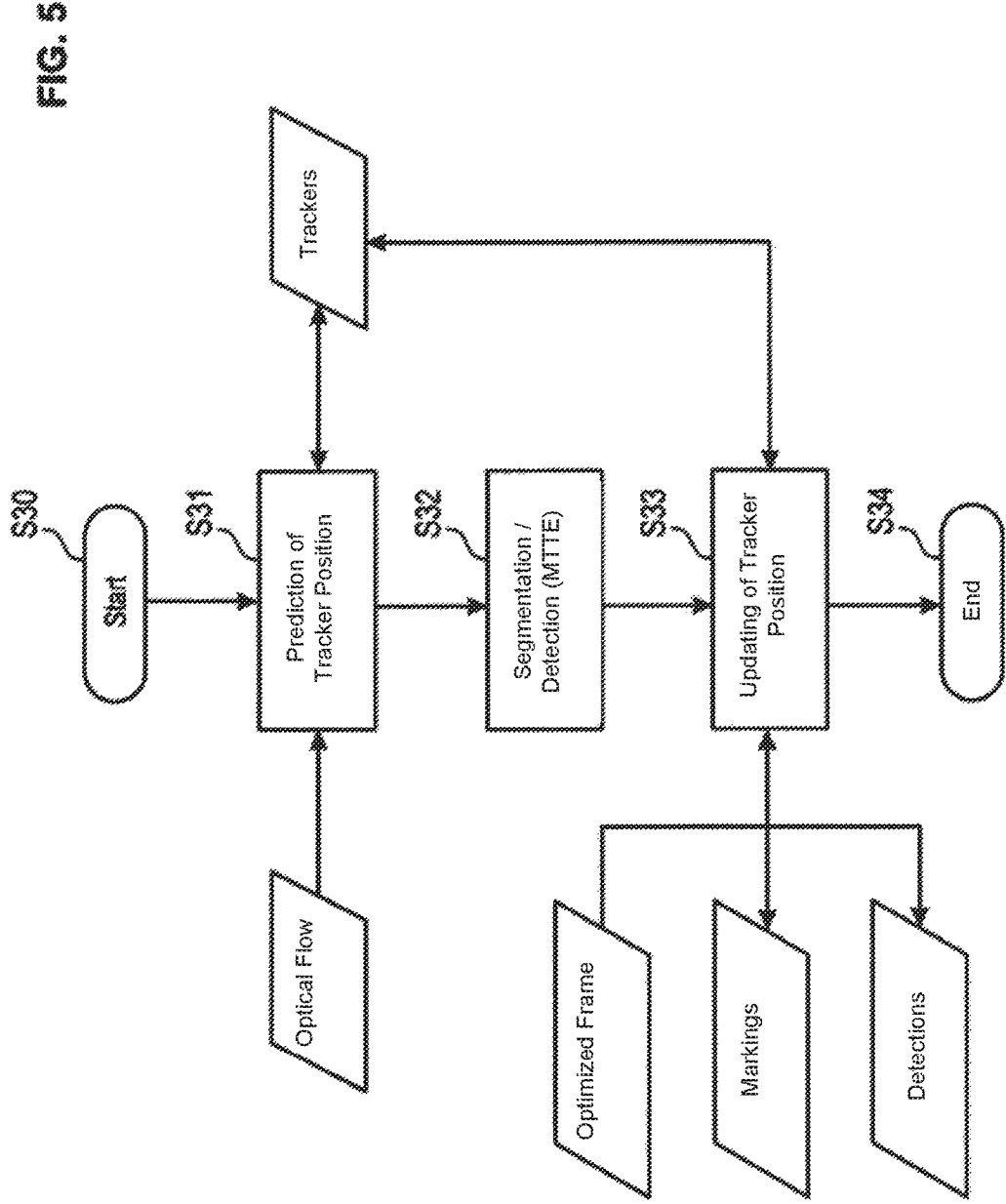
FIG. 5 is a block diagram showing the process flow of instrument tracking carried out in the method of the invention.

The operating principle of modules 36 to 50 included in image processing unit 22 will be apparent in the following from the flow charts shown in FIGS. 3, 4 and 5, which illustrate the image processing according to the invention by way of example. In FIGS. 3 to 5, rectangular symbols denote the processing steps performed by the respective modules, while diamond-shaped symbols represent storage and read-out operations.

The flow chart of FIG. 3 depicts image preprocessing as carried out according to the invention, in which preprocessing module 36, parameter optimization module 38 and flow module 40 of image processing unit 22 are used, in particular.

In step S1, preprocessing module 36, parameter optimization module 38 and flow module 40 receive a buffered frame of the image sequence contained in the video signal. In the present exemplary embodiment, it is assumed in the following that said frame is a conventionally produced individual RGB image, frequently often referred to as an RGB frame.

In step S2, preprocessing module 36 performs various adjustments and optimizations of the RGB frame, aimed at adjusting the image size, brightness and contrast appropriately, for example. In particular, if necessary, preprocessing module 36 also performs an automatic white balance adjustment in step S2. Whether or not a white balance adjustment is performed in S2 is determined in step S3 by parameter optimization module 38 via an actuation signal AWB Y/N, which parameter optimization module 38 supplies to preprocessing module 36. For this purpose, parameter optimization module 38 performs a corresponding check of the image sequence supplied to it. Parameter optimization module 38 operates asynchronously to preprocessing module 36 as part of an iterative parameter optimization, for example in that it does not perform the aforementioned check for each frame.

In step S2, preprocessing module 36 also detects a camera mask in the frame, which represents an image area that cannot be analyzed. Preprocessing module 36 then stores the corresponding mask information which enables the non-usable image area that corresponds to the mask to be filtered out of the frame, as it were, as the process continues.

Once the frame has been optimized in step S2 for further processing, it is stored in an image memory.

In step S4, preprocessing module 36 uses the RGB frame to calculate a grayscale image, the pixels of which are each assigned a grayscale value that represents the color saturation of the corresponding pixel of the RGB frame. The grayscale image generated in step S4 is thus a color saturation image. In S4, this color saturation image is stored for subsequent processing steps.

In step S5, preprocessing module 36 performs a quality check of the RGB frame. If this quality check results in a negative assessment, the RGB frame is discarded and processing continues with the next frame. In contrast, if the quality of the RGB frame is assessed as positive in step S5, then preprocessing ends and the process flow continues with the processing steps according to FIG. 4.

In step S6 according to FIG. 3, a process that runs in parallel with the process steps described above is executed by flow module 40. Flow module 40 is designed to detect the optical flow of the image sequence contained in the video signal. The optical flow represents movement information contained in the image sequence, for example in the form of a vector field that indicates the magnitude and direction of the speed of pixels in the image sequence. In detecting the optical flow, in addition to considering the current RGB frame, flow module 40 also considers the preceding RGB frame. The detected optical flow is then stored. A comparison with previous detection results is also carried out in step S6.

In step S7, the preprocessing according to FIG. 3 ends.

The image processing shown in FIG. 4 is carried out in image processing unit 22 primarily by tracking module 46, which comprises the two submodules 42, 44, by segmentation module 48 and by instrument detection module 50. After image processing starts in step S11, in step S12 segmentation module 48 reads in the grayscale image that was calculated and stored by preprocessing module 36, on the basis of the RGB frame, in step S4 of FIG. 3. Based on this grayscale image, segmentation module 48 generates N binary images using different threshold values, which are predefined, for example, by parameter optimization module 38. Each of these threshold values corresponds to a predefined color saturation, with which the grayscale values of the pixels of the grayscale image are compared. Those pixels of the grayscale image whose grayscale values are equal to or less than the threshold value that corresponds to the predefined color saturation are assigned binary pixels that have a first binary value (for example, 1) in the respective binary image. Correspondingly, those pixels of the grayscale image whose grayscale values are greater than the threshold value are assigned binary pixels that have a second binary value (for example, 0) in the respective binary image. Such a binary image generated in step S12 is shown purely by way of example in FIG. 6, in which binary pixels having a binary value of 1 are assigned the color white and binary pixels having a binary value of 0 are assigned the color black. For purposes of illustration, in FIG. 6 the color black is indicated as dots. Thus, in the binary image of FIG. 6, white image segments represent image areas in which the color saturation is equal to or less than the respectively predefined color saturation. In contrast, black image segments represent image areas in which the color saturation is greater than the predefined color saturation. Since the image processing according to the invention assumes that the color saturation of the instruments to be identified in the video image is lower than that of the anatomical structure being treated, in the binary image of FIG. 6 the white image segments represent the instruments to be identified, while the black image segments represent the anatomical structure.

Figure 6:
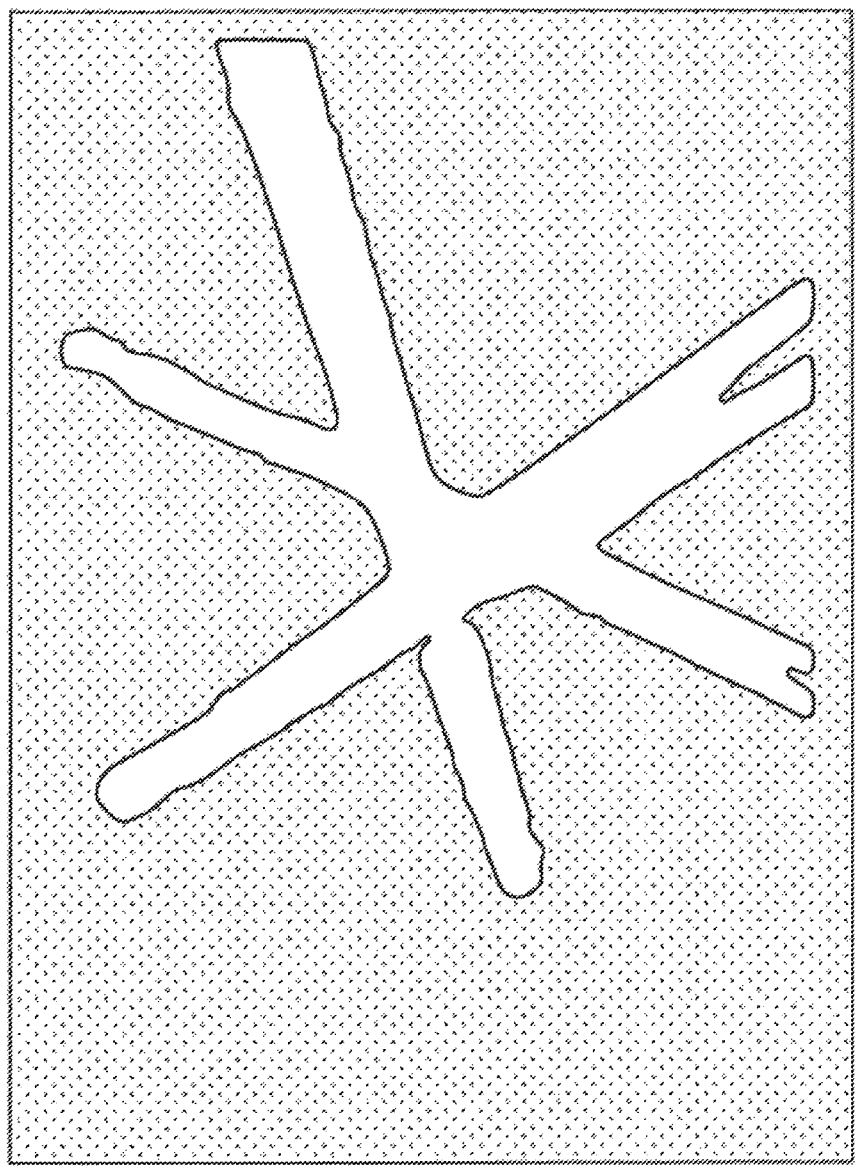
FIG. 6 is a binary image generated in the method of the invention.

In step S12, segmentation module 48 therefore generates N binary images of the type shown in FIG. 6, however these images differ more or less from one another, since they are based on N different threshold values. The greater the difference between the N threshold values, the more the binary images generated using these threshold values will differ from one another.

In step S13, instrument detection module 50 extracts outlines from each of the N binary images and stores these in N outline data sets. In the exemplary binary image of FIG. 6, these outlines extend at the junctions between the white and black image segments.

In step S14, instrument detection module 50 uses the N outline data sets to identify rectilinear sections, hereinafter referred to as line segments. Instrument detection module 50 stores the identified line segments in N line segment data sets.

Figure 7:
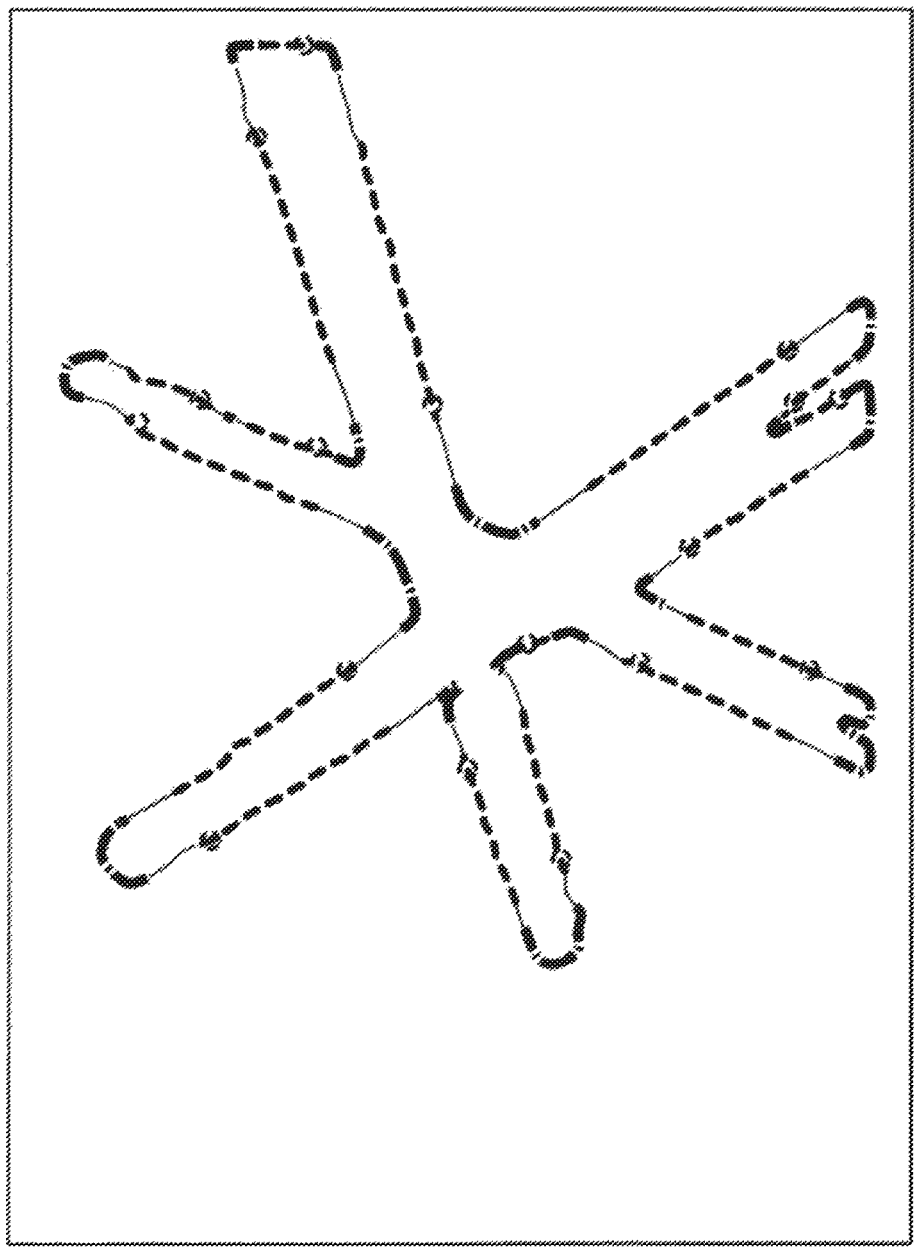
FIG. 7 is an outline obtained from the binary image of FIG. 6.

The process step according to S14 is illustrated in the diagram of FIG. 7. There, the line segments are shown as dashed lines.

In step S14, instrument detection module 50 also detects curved sections of the outlines, to eliminate these from the outlines to be further processed. These curved sections are shown as dotted-dashed lines in FIG. 7.

To avoid any adulteration by the camera mask, in step S14 instrument detection module 50 factors in the mask information that was ascertained and stored by preprocessing module 36 in step S2 of FIG. 2.

Proceeding from the N line segment data sets generated in step S14, in step S15 the instrument detection module 50 generates a single data set in which mutually corresponding line segments from the N binary images are combined to form a single line segment. This composite line segment, also referred to in the following as a compact line segment, represents an edge line of the instrument that results, as it were, from the superimposition of all N binary images. In step S15, based on predefined criteria, instrument detection module 50 ascertains whether line segments identified in the N binary images correspond to one another in the sense described above.

One example of such a criterion is the parallelism of the line segments in question. For example, an angle may be specified as a threshold value, and a check may be made to determine whether the line segments in question have an angular deviation in their alignment that is below this threshold value. If so, the criterion of parallelism is considered to be met. A further criterion may be, for example, a so-called overlap, for which a threshold value can again be predefined. If the segments in question have an overlap with one another that exceeds this threshold value, this criterion is also considered to be met. A further criterion may be, for example, the distance between the line segments in question. If this value is below a predefined threshold value, this criterion is considered to be met. The grayscale value combined with the aforementioned segment spacing also represents a suitable criterion.

The above criteria are essentially aimed at reliably determining whether the line segments in question occur along one and the same gradient within the grayscale image that forms the basis for the N binary images.

Thus, in step S15 the instrument detection module filters the result set generated in step S14 based on the criteria described above.

In step S16, instrument detection module 50 produces edge lines from the compact line segments in which mutually corresponding line segments are combined. Said edge lines represent the edges of the detected instrument. In so doing, instrument detection module 50 factors in detection results that were obtained from the preceding frame.

In step S17, instrument detection module 50 performs a pairing of two edge lines that are arranged parallel to one another and were ascertained in step S16. Once again, this edge pairing is performed on the basis of predefined criteria. One example of such criteria is the orientation of two vectors that extend perpendicular to each of the two edge lines in question.

In process step S17, information regarding the positions of instruments from the preceding frame is used. Also taken into account are position data from so-called trackers, each of which is regarded as a representation of an instrument detected in the frame.

Typically, it is not possible to pair each edge with a different edge in step S17. Therefore, in step S18, instrument detection module 50 assigns leftover edges to supposed instruments located near the edge of the frame. For this purpose, the instrument detection module again factors in the mask information provided in step S2 of FIG. 3.

In step S19, instrument detection module 50 determines the instrument axis as well as the length and orientation of the associated instrument based on a respective edge pair.

In step S20, instrument detection module 50 identifies the tip of the instrument, factoring in geometric characteristics that instrument detection module 50 assumes from the outset as given. One such geometric characteristic might be, for example, a conical shape of the instrument, assumed from the outset. The detection results obtained in step S20 are stored for further use in the subsequent processing steps.

In step S21, instrument detection module 50 filters out false-positively identified instruments. One criterion that may be applied for this purpose is the quality of the edge pairing, for example. Presupposed regularities of certain color properties may also be applied as a criterion. For example, a certain color property exists either in an instrument or in the anatomical structure, but not in the instrument and in the anatomical structure. By factoring in such a regularity, false-positively identified instruments can be filtered out.

Image processing according to FIG. 4 ends with step S22.

The image processing according to FIG. 4 results in stored information about the length, orientation and position of the instrument tip. Supplemental information, for example about the quality of the edge pairing, is also provided.

FIG. 5 is a flow chart depicting the functioning of tracking module 46, which is contained in image processing unit 22 and comprises the two submodules 42 and 44.

After starting in step S30, in step S31 the first submodule 42 of tracking module 46 corrects the positions of the trackers ascertained in the last frame, on the basis of the optical flow detected by flow module 40 in step S6 of FIG. 3. In this process, the first submodule 42 makes a prediction as to where the trackers will move to in the present frame. This prediction of the tracker movement serves to prevent gaps and jumps.

In step S32, segmentation module 48 and instrument detection module 50 then perform the processing steps shown in FIG. 4 for the present frame.

In step S33, the second submodule 44 of tracking module 46 updates the positions of the trackers based on the detection results obtained in step S20 of FIG. 4, and generates new trackers when needed, if new instruments are detected in the frame. The second submodule 44 thereby verifies the prediction of the tracker positions made by the first submodule 42 in step S31. By applying certain criteria, the second submodule 44 determines the reliability of the trackers currently in use.

In step S33, the second submodule 44 assigns markers (labels) to the trackers, which are then displayed on display unit 18, for example, in different colors. Such a marking of different trackers is advantageous, for example, when an instrument that is first being tracked by a particular tracker A drops out of tracking, causing tracker A to be deleted, and ultimately tracking of the same instrument is begun again so that a new tracker B is generated for this purpose. In that case, the two trackers A and B are assigned one and the same marker.

The second submodule 44 then stores the detection results for the next run-through in step S33.

The process according to FIG. 5 ends in step S34.

The image processing described above in reference to FIGS. 3 to 5 is to be understood merely as an example. For instance, it is not absolutely necessary to generate multiple binary images based on the respective grayscale image using different threshold values. Often, the generation of a single binary image using a suitably chosen threshold value is sufficient for separating image segments of low color saturation, which represent an instrument in the frame, from image segments of high color saturation, which represent the anatomical structure. This is true, for example, in cases in which only instruments made of the same material and thus having the same color saturation are used.

It will be apparent to those skilled in the art that various modifications and variations can be made to the present disclosure without departing from the scope of the disclosure. Other embodiments of the disclosure will be apparent to those skilled in the art from consideration of the specification and practice of the teachings disclosed herein. It is intended that the specification and embodiments described herein be considered as exemplary only.

We claim:

1. An assistance device for providing imaging support to an operating surgeon during a surgical procedure involving at least one medical instrument, said assistance device comprising:

a camera for generating a video signal that contains a sequence of image frames;

a display unit for displaying the sequence of image frames on the basis of the video signal;

an image processing unit having an instrument detection module for detecting at least one target structure that represents the instrument being used in a frame of the sequence of image frames by identifying a predetermined distinguishing feature and extracting position information that indicates a position of the target structure in the frame;

a manipulator, which is coupled to the camera and can be actuated via a control signal to move the camera; and a manipulator controller for generating the control signal from the position information and for actuating the manipulator via the control signal;

wherein the instrument detection module identifies an image segment as the predetermined distinguishing feature, said image segment being characterized by a color saturation that is equal to or less than a predefined color saturation, and by an outline that delimits the image segment and has at least one rectilinear section, wherein the image processing unit includes a segmentation module, which generates a plurality of binary images on the basis of the frame of the sequence of image frames, wherein the instrument detection module identifies mutually corresponding rectilinear sections in the binary images and combines these sections to form a composite line segment as the image segment which represents an edge line of the instrument, and wherein the segmentation module generates the plurality of binary images on the basis of a grayscale image generated by a preprocessing module of the image processing unit based on the frame of the sequence of image frames, and applies different threshold values to the grayscale image for the generation of said binary images.

2. The assistance device according to claim 1, wherein the preprocessing module generates the at least one grayscale image on the basis of the frame of the sequence of image frames, the pixels of which are each assigned a grayscale value that represents the color saturation of the corresponding pixel of the frame; and on the basis of the grayscale image, the segmentation module generates the at least one binary image, the binary pixels of which are assigned a first binary value if the associated grayscale values are equal to or less than a threshold value that corresponds to the predefined color saturation, and the binary pixels of which are assigned a second binary value if the associated grayscale values are greater than the threshold value.

3. The assistance device according to claim 1, wherein the instrument detection module combines a plurality of collinearly spaced rectilinear sections of the outline to form a continuous edge line that represents an edge of the instrument.

4. The assistance device according to claim 3, wherein for detection of the target structure, the instrument detection module pairs two edge lines that are arranged parallel to one another in each case.

5. The assistance device according to claim 4, wherein the instrument detection module identifies an instrument tip on the basis of the two paired edge lines.

6. The assistance device according to claim 1, wherein the image processing unit includes a tracking module, which tracks the target structure detected by the instrument detection module over multiple successive frames; and the manipulator controller generates the control signal related to the frame of the sequence of image frames, using the position information about the target structure, for the purpose of actuating the manipulator only if said target structure has already been tracked by the tracking module over multiple successive frames.

7. The assistance device according to claim 6, wherein the tracking module assigns a tracker to a target structure that is detected for the first time in the frame of the sequence of image frames by the instrument detection module, and uses the tracker to track said target structure that is detected in the subsequent frames.

8. The assistance device according to claim 1, wherein the image processing unit includes a flow module, which detects an optical flow of the image sequence, which represents movement information contained in the image sequence.

9. The assistance device according to claim 6, wherein the tracking module comprises a first submodule, located upstream of the instrument detection module, and a second submodule, located downstream of the instrument detection module;

the first submodule factors in the optical flow detected by the flow module to make a prediction regarding the position information about the tracker for the next frame, which has not yet been processed by the instrument detection module;

and for said next frame, which has been processed by the instrument detection module, the second submodule verifies the prediction made by the first submodule based on the position information for the tracker detected by the instrument detection module.

10. The assistance device according to claim 2, wherein the preprocessing module is designed to perform a white balance adjustment of the frame of the sequence of image frames.

11. The assistance device according to claim 10, wherein the image processing unit includes a parameter optimization module, which processes the frames asynchronously to the preprocessing module and from them generates actuation information, which specifies whether or not the preprocessing module should perform the white balance adjustment.

12. The assistance device according to claim 11, wherein the parameter optimization module predefines the threshold values for the segmentation module on the basis of the asynchronous processing of the frames.

13. A method for providing imaging support to an operating surgeon during a surgical procedure involving at least one medical instrument, comprising:

generating, with a camera, a video signal that includes a sequence of image frames;

displaying the image sequence on a display unit on the basis of the video signal;

detecting at least one target structure that represents the instrument being used in a frame of the sequence of image frames by identifying a predefined distinguishing feature, and position information that indicates a position of the target structure in the frame;

generating a control signal from the position information, and actuating a manipulator coupled to the camera via the control signal to move the camera;

wherein an image segment is identified as the predefined distinguishing feature, said image segment being characterized by a color saturation that is equal to or less than a predefined color saturation, and by an outline that delimits the image segment and has at least one rectilinear section, wherein the image segment is identified by generating a plurality of binary images on the basis of the frame of the sequence of image frames, identifying mutually corresponding rectilinear sections in the binary images, and combining these sections to form a composite line segment as the image segment which represents an edge line of the instrument, and wherein the plurality of binary images are generated on the basis of a grayscale image generated by a preprocessing module based on the frame of the sequence of image frames by applying different threshold values to the grayscale image for the generation of said binary images.

* * * * *